United States Patent [19]

Shum et al.

[11] Patent Number: 4,687,868

[45] Date of Patent: Aug. 18, 1987

[54] PRODUCTION OF MOLYBDENUM DIOXO DIALKYLENEGLYCOLATE COMPOSITIONS FOR EPOXIDATION OF OLEFINS

[75] Inventors: Wilfred P. Shum, Swarthmore; Charles F. Cooper, Paoli, both of Pa.

[73] Assignee: Atlantic Richfield Company, Los Angeles, Calif.

[21] Appl. No.: 854,953

[22] Filed: Apr. 23, 1986

Related U.S. Application Data

[63] Division of Ser. No. 668,057, Nov. 5, 1984, Pat. No 4,607,113.

[51] Int. Cl.[4] .............................................. C07F 11/00
[52] U.S. Cl. .................................... 556/57; 502/167; 549/533
[58] Field of Search ........................................ 556/57

[56] References Cited

U.S. PATENT DOCUMENTS 2,795,552 6/1957 Abbott et al. .
3,285,942 11/1966 Price et al. .
3,351,635 11/1967 Kollar .
3,434,975 3/1969 Sheng et al. .
3,453,218 7/1969 Sheng et al. .
3,480,563 11/1969 Bonetti et al. .
3,668,227 6/1972 Mattuci et al. .
3,822,321 7/1974 Maurin .
3,956,180 5/1976 Cavitt .
3,991,090 11/1976 Hagstrom et al. .
4,009,122 2/1977 Lines et al. .
4,046,783 9/1977 Cavitt .
4,157,346 6/1979 Lines et al. .

FOREIGN PATENT DOCUMENTS 1550166 11/1968 France .

OTHER PUBLICATIONS

Chemical Abstracts 97 7286j (1982).

Primary Examiner—Helen M. S. Sneed
Attorney, Agent, or Firm—Michael S. Jarosz

[57] ABSTRACT

Production of novel molybdenum dioxo dialkyleneglycolate compositions, especially adapted for use as catalysts in the epoxidation of olefinic compounds with an organic hydroperoxide, by reaction of molybdenum trioxide with particular dialkylene glycol compounds at specified elevated temperatures while removing water.

5 Claims, 1 Drawing Figure

PRODUCTION OF MOLYBDENUM DIOXO DIALKYLENEGLYCOLATE COMPOSITIONS FOR EPOXIDATION OF OLEFINS

This is a division of application Ser. No. 668,057, filed Nov. 5, 1984.

BACKGROUND OF THE INVENTION

The production of oxirane compounds such as propylene oxide and its higher homologs is described in Kollar U.S. Pat. No. 3,351,635. In accordance with the Kollar process, the oxirane compound may be prepared by epoxidation of an olefinically unsaturated compound (for example, propylene) by use of organic hydroperoxide and a suitable metal catalyst, such as a molybdenum compound. Kollar teaches that activity of the metal catalyst disclosed therein for expoxidation of primary olefins is high and can lead to high selectivity of propylene to propylene oxide. These selectivities ar obtained at high conversions of hydroperoxide (50% or higher) which conversion levels are important for commercial utilization of this technology. In accordance with the Kollar process, the epoxidation reaction proceeds under pressure in a liquid state, and accordingly, a liquid solution of the metal catalyst is desired.

In the preparation of these compounds, for example, molybdenum salts, for the aforementioned purpose, various techniques have been used, many of which have been found to be extremely difficult to carry out efficiently on a commercial scale, and hence expensive, particularly for preparing hydrocarbon soluble compositions containing a high molybdenum content. In addition, a number of the above-identified catalyst materials suffer from various disadvantages including poor solubility in the reaction medium and low metal concentration.

Although preparations of epoxidation catalysts from molybdenum metal have been reported in the prior art, for example, in Sheng et al U.S. Pat. Nos. 3,453,218 and 3,434,975, in an effort to increase the amount of catalyst metal carried to the reaction medium in the catalytic epoxidation of olefins, however, the use of low cost starting materials, such as molybdenum trioxide, in the preparation of epoxidation catalyst solutions soluble in hydrocarbons has been hampered due to the slow rate of dissolution, precipitation of solids as a result of decomposition of the dissolved molybdenum species, and unsatisfactory low molybdenum concentration in these solutions. Accordingly, a number of preparations of organic-soluble molybdenum containing catalysts from a variety of oxygen containing molybdenum compounds have been reported in the prior art. In this connection, attention is directed to Bonetti U.S. Pat. No. 3,480,563 which discloses the preparation of such catalysts by reacting molybdenum trioxide with a monohydric primary saturated acyclic alcohol having from 4 to 22 carbon atoms in the molecule or with a mono- or polyalkylene glycol monoalkyl ether or mixtures thereof. An earlier patent to Price et al, U.S. Pat. No. 3,285,942 discloses the preparation of glycol molybdates of specified formula by reaction of an alpha- and beta-alkane diols of from 2 to 18 carbon atoms with molybdic acid or related molybdenum compounds in the presence of an organic nitrogen base. Maurin et al U.S. Pat. No. 3,822,321 describes the oxidation of olefins with a hydroperoxide using a molybdenum catalyst prepared by reaction of molybdenum containing compound, such a molybdic acid or salt, with a polyalcohol. A molybdenum catalyzed epoxidation of olefins is also described by Lines et al in U.S. Pat. No. 4,157,346. The catalyst is prepared by reacting an oxygen-containing molybdenum compound with amine (or an amine N-oxide) and alkylene glycol. Hagstrom et al U.S. Pat. Nos. 3,991,090 and 4,009,122 dislcose a method of preparing molybdenum compound by reaction of an oxygen containing molybdenum compound with a polyhydroxy compound having vicinal hydroxyl groups in the presence of a hydrohalic acid. French Pat. No. 1,550,166 discloses that molybdic acid esters, and especially glycol esters of molybdic acid, provide certain advantages over previously known catalysts to effect epoxidation employing organic hydroperoxides in reaction with olefinic compounds. Cavitt U.S. Pat. No. 4,046,783 discloses the use in olefin epoxidation reactions of an oxidized alkyl molybdate complex catalyst prepared by contacting an inorganic molybdenum compound with an aliphatic monohydric alcohol in the presence of a weak base to form a lower oligomeric alkyl molybdate compound which is then oxidized to form an oxidized alkyl molybdate complex catalyst. Also, ammonium molybdate epoxidation catalyst solutions are described in U.S. Pat. Nos. 3,956,180 and 2,795,552.

Accordingly, it is an object of the present invention to provide a process for the production of novel molybdenum dioxo dialkyleneglycolate compositions from molybdenum trioxide by a simple, inexpensive method.

A further object of the present invention is to provide molybdenum-containing catalyst compositions based on novel dioxo dialkyleneglycolate compounds which compositions are characterized by improved dissolution rates in organic hydrocarbon solutions, high molybenum concentrations in organic solutions, and provide stable dissolved molybdenum species free of precipitation of solids due to decomposition, thereby providing improved and increased catalyst preparation and productivity.

An additional object of the present invention is to provide a process for the epoxidation of olefinic compounds by use of the molybdenum dioxo dialkyleneglycolate catalyst compositions of the invention, thereby resulting in increased selectivity to desired alkylene oxide, e.g. propylene oxide, product in the epoxidation of a primary olefin, e.g. propylene, while at the same time reducing production of undesired by-products.

SUMMARY OF THE INVENTION

It has now been discovered that stable solutions of molybdenum-containing epoxidation catalyst compositions, present in the form of a novel molybdenum dioxo dialkyleneglycolate compounds and which contain increased quantities of molybdenum in such catalyst composition than heretofore obtainable, may be prepared by reacting commercially available molybdenum trioxide with a specified dialkyleneglycol at certain specified elevated temperatures while removing water. Accordingly, it has been discovered, in accordance with the present invention, that a relatively inexpensive source of molybdenum, namely molybdenum trioxide, may be directly reacted with the aforedescribed class of dialkyleneglycols under certain controlled reaction conditions to produce a novel class of molybdenum dioxo dialkyleneglycolate compounds which are particularly stable in organic solutions and capable of providing high molybdenum content in resulting catalyst compositions, thereby rendering the same especially adapted for use as catalysts in the epoxidation of olefinic compounds with an organic hydroperoxide oxidizing agent. A further advantage of the present invention comprises the production of a novel class of molybdenum compounds, namely molybdenum dioxo dialkyleneglycolates by a simple heating step, without any further processing, from commercially available, inexpensive molybdenum trioxide.

DETAILED DESCRIPTION OF THE INVENTION

Figure 1:
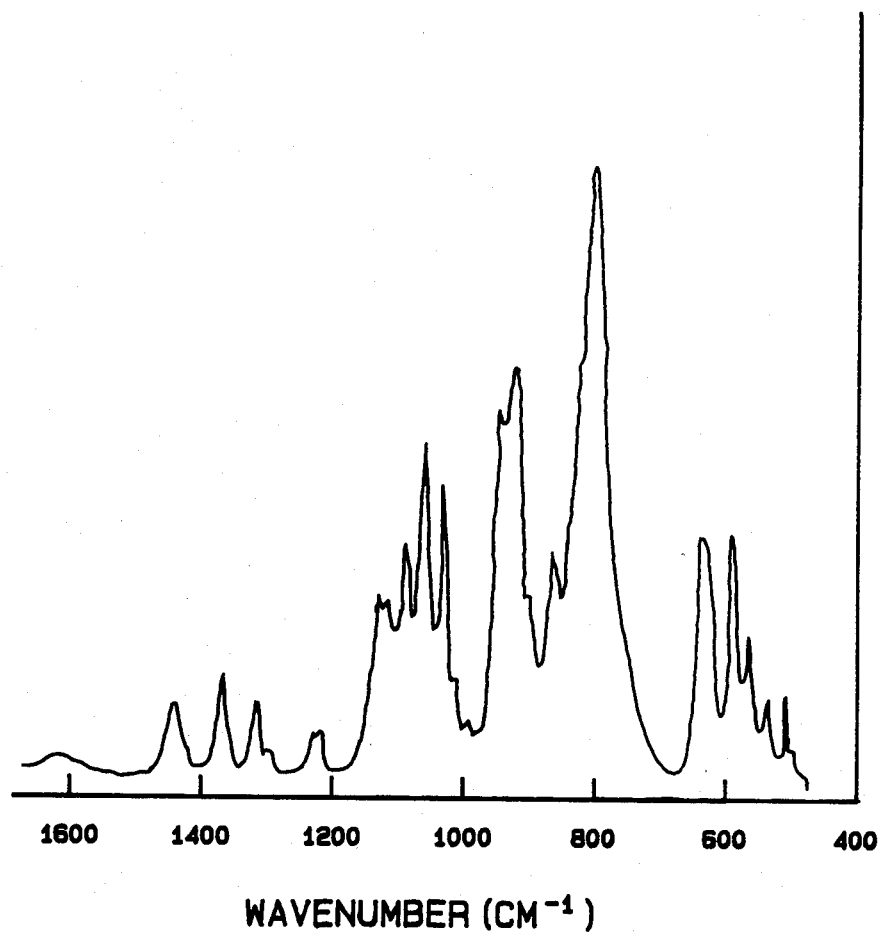

The molybdenum dioxo dialkyleneglycolate compounds of the present invention correspond to the formula:

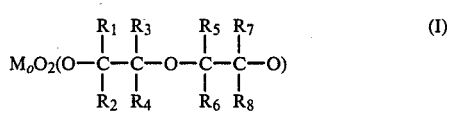
(I)

wherein at least one member of $R_1$ through $R_4$ and at least one member of $R_5$ through $R_8$ is an alkyl radical of 1 to 4 carbon atoms and the remaining members of $R_1$ through $R_4$ and $R_5$ through $R_8$ are each independently selected from the group consisting of hydrogen or an alkyl radical of 1 to 4 carbon atoms. Preferred dialkyleneglycolate compounds of the present invention conform to above Formula I wherein not more than one member of $R_1$ through $R_4$ and not more than one member of $R_5$ through $R_8$ is methyl and the remaining members of $R_1$ through $R_4$ and $R_5$ through $R_8$ are hydrogen, which compounds may generally be referred to as molybdenum dioxo dipropyleneglycolates, because of the particularly high molybdenum content contained therein and stability characteristics, i.e. lack of precipitation of solids due to decomposition of the dissolved molybdenum species. The dialkyleneglycolate compounds of the invention, may be present as individual distinct compound species or as admixtures of compound isomers conforming to Formula I, above, depending upon the isomeric purity of dialkylene glycol starting material employed in the preparatory method of the invention, described in more detail below. Representative compounds of the present invention other than the aforementioned dipropyleneglycolate include: molybdenum dioxo dibutyleneglycolate; molybdenum dioxo dipentyleneglycolate and molybdenum dioxo dihexyleneglycolate. The molybdenum dioxo dialkyleneglycolate compounds of the invention are further characterized as containing a molybdenum:oxygen:ligand ratio of 1:2:1. These compounds, in general, may be characterized as clear, homogeneous, light yellow solutions which are capable of containing up to about 15% of dissolved molybdenum, generally between about 8 and 12% of dissolved molybdenum, in organic solutions.

As used in the present specification and the annexed claims, the term "stable catalyst solution" is intended to mean a molybdenum-containing solution which will not precipitate an appreciable amount, less than about 0.1% of the molybdenum contained in the solution, of molybdenum, upon heating to a temperature of about 50° C. over a period of at least 4 hours, followed by standing at ambient temperature for at least 24 hours.

The process of the present invention directed to the preparation of the dialkyleneglycolate compounds comprises the direct reaction of molybdenum trioxide with a dialkyleneglycol compound corresponding to the formula:

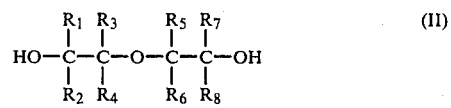
(II)

wherein $R_1$ through $R_4$ and $R_5$ through $R_8$ are as above indicated, while removing water from the reaction mixture, thereby forming the desired liquid molybdenum dioxo dialkyleneglycolate compound. It is a critical feature of the present process that free water be removed during the reaction; this includes any water that may be initially present, as well as water that might be formed during the reaction.

The dialkyleneglycols contemplated for use in the aforedescribed process for preparation of the dialkyleneglycolate compounds may comprise any of the aforedescribed dialkyleneglycols which are liquid at atmospheric pressure at temperatures up to about 150° C. These dialkylene glycols, in general, correspond to above-identified Formula II, and, as indicated above, may be present as an individual distinct isomer species, or as an isomeric mixture of dialkylene glycols. Commercially available dipropylene glycol, a colorless, odorless liquid of low volatility constitutes a particularly preferred dialkyleneglycol for use in the process of the invention. Alternatively, mixtures of dialkyleneglycols may be employed in the reaction with molybdenum trioxide in the production of mixed molybdenum dioxo dialkyleneglycolate compounds of the invention.

As indicated previously, removal of water is a critical feature of the process for preparation of the dialkyleneglycolate compounds of the invention. If the reaction is carried out without the removal of water, extremely long reaction times may be required in preparation of these glycolate compounds and, more importantly, the stability of the resultant dialkyleneglycolate compound or admixture may not be achieved. However, although water removal appears necessary, the manner in which water is removed is unimportant. Therefore, one may employ any known technique for water removal during this preparatory reaction. A particularly desirable manner in which water may be removed from the reaction mixture and which significantly reduces the reaction time for formation of the desired molybdenum glycolate compound involves employment, in conventional manner, of a gas purge comprising a molecular oxygen-containing gas, such as air, or an inert gas, such as nitrogen. Particularly preferred is use of a molecular oxygen-containing gas, purge, for example, air, which not only removes water in the reaction mixture, but also maintains dissolved molybdenum in its higher oxidation state, thus allowing for higher loading of molybdenum in the resultant molybdenum glycolate solution. In the absence of sufficient oxygen, or air, reduction of the molybdenum glycolate complex occurs, forming dark blue colloidal solutions which are capable of being oxidized by air, or a molecular oxygen-containing gas, at elevated temperatures, generally between about 120° C. and 150° C. In general, any amount of oxygen sufficient to reoxidize the reduced low valent molybdenum of the reduced molybdenum compound to hexavalent molybdenum may be employed. Alternatively, water may be removed by the use of dehydrating agents, such as calcium chloride, or by use of an azeotropic agent. Any azeotropic agent which is inert to the reaction itself may be employed in the process. Suitable azeotropic compounds include benzene or arylalkyl compounds, such as lower alkyl benzenes containing of from 1 to 3 alkyl groups and each alkyl group containing of from 1 to 4 carbon atoms, such as ethylbenzene, xylene, cumene, or any other straight or branched chain hydrocarbon, such as an alkane of from 5 to 12 carbon atoms, e.g. hexane, octane and decane. The quantity of azeotropic agent necessary depends upon the amount of water to be removed and will vary from one system to another, which quantity can be readily determined by one skilled in the art. In general, it may not be necessary to remove all water which is present in or may be formed during the reaction. The amount of water removed will depend upon the weight concentration of molybdenum desired in the dialkyleneglycolate compound(s) produced and the duration of the reaction. The more concentrated molybdenum-containing glycolate solutions to be produced in the reaction will require removal of greater guantities of water, with removal of substantially all water present or formed during the reaction being optimum for obtaining the most concentrated molybdenum containing glycolate compositions; hence, such procedure will provide reaction mixtures containing up to about 1%, generally up to about 0.5%, and preferably, up to about 0.1%, by weight of water, based on the weight of the reaction mixture.

The reaction between molybdenum trioxide and dialkylene glycol should be controlled at a temperature of from about 100° C. to about 150° C. In its preferred aspects, the reaction is carried out at a temperature of from about 120° C. to about 140° C., and especially between about 125° C. and 135° C. Any minimum temperature which provides the desired reaction may be employed, but temperatures higher than about 150° C. are not recommended due to the susceptibility of dissolved molybdenum dialkylene-glycolate complex to thermally decompose at such temperatures, forming dark brown solutions which are not completely homogeneous, and hence, incapable of forming stable catalyst solutions. It is particularly convenient to use atmospheric pressure reflux temperatures of the reaction mixture as the reaction temperature, although pressures above atmospheric may also be employed; is desired. With increase in temperature, shorter reaction times may be employed, although, in general, reaction times in the range of from about 2 to 24 hours, or longer, preferably 4 to 10 hours, are sufficient to produce the desired organic soluble molybdenum glycolate compound.

The quantity of molybdenum trioxide employed for reaction with the dialkylene glycol may range from about 5 weight percent to about 35 weight percent of glycol, with amounts ranging from about 10 weight percent to about 25 weight percent being preferred. In general, the molybdenum dioxo dialkyleneglycolate compositions of the invention contain of from about 5 to about 15 percent molybdenum, based on the weight of the composition.

The molybdenum-containing compositions prepared in accordance with the process of the present invention have been found to be suitable as catalysts for epoxidation of olefins, illustratively propylene, to produce the corresponding oxirane compound, e.g., propylene oxide, for example, at high yields and conversions, without production of high quantities of undesirable by-products. In general, the compositions of the present invention when employed in conventional manner and connect as is known in the art, are suitable as catalysts in the epoxidation of olefinic compounds having the general formula:

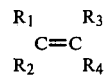

where $R_1$, $R_2$, $R_3$ and $R_4$ may be hydrogen, alkyl, aryl arylalkyl, alkaryl, alkenyl, alkadienyl or similar radicals having functional groups, in accordance with the process described and claimed in Kollar U.S. Pat. No. 3,351,635, the disclosure of which is hereby incorporated by reference. Illustrative acylic olefinic hydrocarbons which may be epoxidized are the aliphatic normally gaseous olefins such as propylene, the butylenes and the higher liquid and solid olefins.

In addition to being employed as fresh catalyst solution in the above-described epoxidation reaction, the molybdenum-containing catalyst composition of the present invention finds particular use as make-up catalyst to be employed together with molybdenum-containing catalyst concentrate or residue. Such concentrations or residues are obtained from previous epoxidation processes employing a molybdenum epoxidation catalyst wherein the epoxidation reaction mixture is resolved into product fractions, including a heavy liquid fraction containing the catalyst, subjecting the heavy liquid fraction containing the catalyst to evaporation, such as a wiped film evaporation, at elevated temperatures until at least about 60% by weight of said fraction is evaporated overhead, and recycling the evaporation residue to said epoxidation, as described and claimed in Levine et al U.S. Pat. No. 3,819,663, the disclosure of which is hereby incorporated by reference. When employed as make-up catalyst, the catalyst composition of the present invention is employed in quantities up to about 90, and preferably up to about 50 percent, by weight, of the catalyst composition being recycled to the epoxidation reaction.

In order to illustrate practice of the invention, the following examples are provided. It is to be understood that the examples are merely illustrative and are not intended to be restrictive of the invention herein disclosed and as defined by the claims following hereto. Parts and percentages are by weight, and temperatures are in degrees Centigrade, unless otherwise specified.

EXAMPLE 1

A mixture of 7.5 parts of molybdenum trioxide and 42.5 parts of dipropylene glycol were heated at 128° with air purging through the reaction mixture at a rate of 0.10 liters per minute over a period of 30 hours. The liquid product, a clear light yellow solution containing 10% dissolved molybdenum, was crystallized from petroleum ether, thereby providing a molybdenum dioxo dipropyleneglycolate corresponding to the formula:

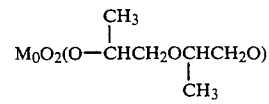

as determined by 13C NMR and X-ray diffraction analysis. The infrared spectrum of the glycolate produced, set forth in FIG. I, shows absorptions from the ligand (dipropyleneglycol) at 1120, 1100, 1080, 1050, 1020 and 860 cm$^{-1}$; characteristic Mo=O adsorptions at 935 and 920 cm$^{-1}$; and Mo O Mo absorption at 800 cm$^{-1}$, indicating oligomerization of the glycolate compound in the solid state. The compound is also characterized by elemental analysis as follows:

Calculated for $C_6H_{12}O_5Mo$; C, 27.7%; H, 4.7%; Mo, 36.9%. Found; C, 28%; H, 4.6%; Mo, 37%.

EXAMPLE 2

A mixture of 5.6 parts of molybdenum trioxide and 44.4 parts of dipropylene glycol were heated at 128° C. with air purging through the reaction mixture at a rate of 0.36 liters per minute. A clear yellow solution containing 7.7% of dissolved molybdenum was obtained after 17 hours. The water concentration in the solution was measured to be less than 0.1%.

EXAMPLE 3

A mixture of 5.6 parts of molybdenum trioxide and 44.4 parts of dipropylene glycol were heated at 130° with a slow purge of nitrogen. After heating overnight, the reaction mixture was a dark blue colloidal solution which, on purging with air at 130° C. at a rate of 0.36 liters per minute, was gradually oxidized to provide a clear yellow solution containing 7.7% of dissolved molybdenum.

EXAMPLE 4

A mixture of 10 parts of reagent grade molybdenum trioxide and 60 parts of dipropylene glycol were heated at 150° for 2 hours. Air was bubbled through the reaction mixture with additional dipropylene glycol being introduced into the reaction vessel as required to maintain a constant liquid level. After cooling to a room temperature, ethylbenzene was added into the reaction mixture to aid in filtration of any remaining undissolved solids. Solids conversion of molybdenum trioxide to desired molybdenum dioxo dipropyleneglycolate was greater than 99.5% and the concentration of soluble molybdenum in the solution was 10.5%.

EXAMPLE 5 (COMPARATIVE)

The process of Example 4, above, was repeated except that, 1,2-monopropylene glycol was employed in lieu of the dipropylene glycol. It was found that solids conversion amounted to only 78.7%, and the final reaction mixture had a dark green color with substantial solids remaining undissolved.

EXAMPLE 6 (COMPARATIVE)

A mixture of 10 parts of reagent grade molybdenum trioxide and 60 parts of diethylene glycol were heated at 160° for one hour. Residual solids obtained were 57% higher than the original charge indicating that precipitation of molybdenum diethyleneglycolate compound had occurred.

EXAMPLE 7 (COMPARATIVE)

The procedure of Example 6, above, was repeated except that tripropylene glycol was employed in lieu of diethylene glycol. The results indicated that solids conversion was only 3%.

EXAMPLE 8 (COMPARATIVE)

A mixture of 2.17 parts of molybdenum trioxide and 25 parts of 2-methoxyethanol was heated at 128° with a slow air purge at 0.36 liters per minute over a period of 65 hours. All of the molybdenum trioxide reacted with the 2-methoxyethanol during this period but some of the reaction product had precipitated from the solution. On cooling the reaction mixture to room temperature, it was found that 3 grams of the molybdenum containing compund was obtained as a solid.

EXAMPLE 9

A stainless steel autoclave equipped with a stirrer was charged with 75 parts of propylene, 75 parts of a solution comprised of about 40% by weight tertiary butyl hydroperoxide in tertiary butyl alcohol and 0.12 parts of a catalyst solution obtained in Example I, above, containing 150 ppm of molybdenum. The epoxidation reaction was effected at 121° C. and 800 psia over a period of time sufficient to obtain a tertiary butyl hydroperoxide conversion of 100%, based on the tertiary butyl hydroperoxide charged. The yield of desired propylene oxide product was 94%.

Examples 1-4 inclusive, show the production of molybdenum dioxo dipropyleneglycolate in accordance with the process of the invention and Example 9 shows that catalysts produced in accordance with this invention utilizing dialkylene glycols for reaction with molybdenum trioxide provide conversions and propylene oxide selectivity at least as good or better than standard organic soluble molybdenum catalysts.

Examples 5 through 8 show that typical ligands of the prior art, monopropylene glycol, diethylene glycol, dipropylene glycol and the diethylene glycol monomethyl ether, fail to yield a stable molybdenum-containing catalyst containing molybdenum in the high molybdenum concentrations which are capable of being obtained by use of the dialkylene glycols of the present invention.

What is claimed is:

1. A molybdenum dioxo dialkyleneglycolate compound of the formula:

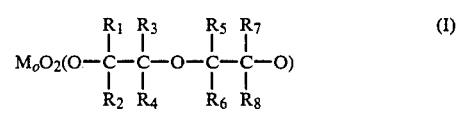

wherein at least one member of $R_1$ through $R_4$ and at least one member of $R_5$ through $R_8$ is an alkyl radical of 1 to 4 carbon atoms and the remaining members of $R_1$ through $R_4$ and $R_5$ through $R_8$ are each independently selected from a group consisting of hydrogen or an alkyl radical of 1 to 4 carbon atoms.

2. The dialkyleneglycolate compound of claim 1 wherein, in said formula, at least one member of $R_1$ through $R_4$ and at least one member of $R_5$ through $R_8$ is methyl and the remaining members of $R_1$ through $R_4$ and $R_5$ through $R_8$ are each independently selected from a group consisting of hydrogen or an alkyl radical of 1 to 4 carbon atoms.

3. The dialkyleneglycolate compound of claim 1 wherein at least one member of $R_1$ through $R_4$ and at least one member of $R_5$ through $R_8$ is methyl and the remaining members of $R_1$ through $R_4$ and $R_5$ through $R_8$ are each hydrogen.

4. The dialkyleneglycolate compound of claim 1 wherein, in said formula, $R_1$ and $R_6$ are each methyl.

5. The dialkyleneglycolate compound of claim 1 wherein, in said formula, $R_1$ and $R_6$ are each methyl, and $R_2$, $R_3$, $R_4$, $R_5$, $R_7$, and $R_8$ are each hydrogen.

* * * * *